US00PP09785P

United States Patent [19]

Saville

[11] Patent Number: Plant 9,785

[45] Date of Patent: Jan. 28, 1997

[54] MINIATURE ROSE PLANT NAMED 'SAVACOOK'

[75] Inventor: F. Harmon Saville, Newburyport, Mass.

[73] Assignee: Nor'East Miniature Roses, Inc., Rowley, Mass.

[21] Appl. No.: 575,282

[22] Filed: Dec. 20, 1995

[51] Int. Cl.[6] ..... A01H 5/00

[52] U.S. Cl. ..... Plt./7.1

[58] Field of Search ..... Plt./7.1, 8.2, 9, Plt./10.1, 22

*Primary Examiner*—Howard J. Locker

[57] ABSTRACT

SAVacook is a miniature rose which can be grown quite satisfactorily in a greenhouse or as a hardy, garden perennial. It blooms continually throughout the growing season with buds and flowers of an apricot-yellow blend. Blooms are most often born in clusters but also singly, making them good for cut flowers. The plant, itself, grows 18 to 24 inches tall in a nice mounded form making it ideal as either a specimen plant or in a border. This variety does need winter protection in severe climates.

1 Drawing Sheet

CROSS REFERENCE

This present invention relates to a new and distinct variety of hardy, bush type plant of the miniature rose class, whose flowers bear some resemblance in color and the way temperature and light intensity effect that color, to those of SAVasilk, U.S. Plant Pat. No. 5,164 (marketed and sold under the name Cornsilk). The flower of the new invention has fewer petals but is slightly larger in size than those of SAVasilk, U.S. Plant Pat. No. 5,164.

BACKGROUND OF THE INVENTION

1. This invention is a rose plant of the miniature rose class which can be grown quite satisfactorily in a greenhouse or as a graden perennial, as a specimen plant, in a border, or for cut flowers, needing protection through the winter in severe climates.

2. This present invention is a new and distinct variety of miniature rose plant (*Rose chinensis 'minima'*), which was created by crossing the following the following two roses: The seed parent is Baby Katie, U.S. Plant Pat. No. 4,471, a compact and prolific miniature rose, whose flowers are a pink to salmon and cream blend, created F. H. Saville in 1978, sold and marketed under the name Baby Katie. The pollen parent is Mazurka, a medium pink, prolific, floribunda rose, created by Verbeck in 1965, not patented. The varietal denomination of this new rose is SAVacook.

This new variety is distinguished by:

Buds and flowers of a soft apricot blend, deriving much of its characteristic color from its seed parent, Baby Katie, U.S. Plant Pat. No. 4,471.

Buds that open in different shades of apricot but that still finish up as the same shade of light yellow to yellow/apricot blend.

Flowers borne in abundance in clusters and one to a stem.

A plant that grows equally well in a greenhouse or outdoors; it's always in bloom to serve as a decorative plant or for cut flowers.

Little or no fragrance.

Asexual production by cuttings of this new variety as performed in Essex County, Mass. and in San Bernardino County, Calif. shows that all distinguishing characteristics of this rose continually come true to form.

SUMMARY OF THE INVENTION

This new variety has flowers of light apricot-yellow blend, borne in abundance in clusters of up to seven flowers and one-to-a-stem. The plant itself grows 18 to 24 inches tall at maturity forming a nice mound to 20 inches wide, being of bushy and compact habit.

BRIEF DESCRIPTION OF THE DRAWING

The accompanying color photograph shows specimen of the flowers of this new variety in different stages of development as seen and grown outside in early September in Essex County, Mass.

BOTANICAL DESCRIPTION OF THE PLANT

Following is a detailed description in outline form pertaining specifically to this new and distinct variety of miniature rose plant. All major color plate identifications made are referring to The Royal Horticulture Society Colour chart except where common terms of color definition are employed.

Type: Miniature rose; hardy; outdoors; decorative; specimen plant; border plant; cut flowers; potted plant; greenhouse.

Seed Parent: Baby Katie, U.S. Plant Pat. No. 4,471.

Pollen Parent: Mazurka, not patented.

Flowers: Usually borne in clusters of up to seven flowers but also singly on stems averaging six inches in length.

Quantity of bloom: Abundant.

Bud:

*Size and form.*—½ of an inch in length; ovoid.

*Sepals.*—Three outer sepals are heavily foliated towards the tips and with some foliation half-way up the sepal edges; near 144A in color; sepals extending beyond the tip of the bud by about ⅓ of the bud length.

*Color when sepals first divide.*—25D, occasionally near 32D.

*When petals begin to unfurl.*—Near 28D with outer edges of 27D.

*Peduncle.*—One and ⅜ inches in length, usually with a slight curve to them; erect; near 144A in color.

*Sepals.*—Bending back to about a 45 degree angle from the stem as the flower opens, holding that position until the petals drop, then coming up to a 90 degree angle, always remaining curled up at the tip.

Bloom:

*Size when fully expanded.*—Averaging 1⅞ inches.

*Form.*—High centered at first, petals becoming loosely rolled outward and remaining that way until dropping from the reeptacle.

*Petalage under normal conditions.*—15 to 20 with 1 to 5 petaloids in the center of the flower.

*Fragrance.*—Occasinally there is a very light, sweet fragrance from the open bloom.

Petals:

*Texture.*—Medium, inside velvety, outside satiny.

*Form.*—Broad fan shaped, although they give the appearance of being ovate with acute tip, once the edges roll outward.

Color: From plants grown outside in Essex County, Mass., in September, 1995.

*During first two days.*—Outer petals: inside surface —near 19D. Reverse —27C. Inner petals: inside surface — near 24D with 6C towards the base of the petals. Reverse — near 28D.

*Base of petals at attachment.*—IIA.

*Color change as bloom ages.*—From 25D or 32D to near 28D and outer edges of 27D, to near 19D and 24D with 6C towards the center of the flower, to all 19D.

*General tonality.*—Light yellow-apricot blend; after three or more days — varying shades of light Apricot.

Lasting quality: On plant—6 to 10 days, before dropping cleanly. As a cut flower—5 to 8 days or longer, depending on temperature.

Reproductive organs:

*Stamens.*—Some, 30–40, arranged in one single row around the top edge of the receptacle, just inside the corolla.

*Filaments.*—Up to 3/16 of an inch in length; light yellow, near 13C.

*Anthers.*—Near 13D in color.

*Pollen.*—Small amount; near 167A in color.

*Pistils.*—About the same amount as stamens.

*Styles.*—Uneven in length, clustered with shortest styles in the very center; some outer styles to 5/32 of an inch.

*Stigmas.*—Color near 4D.

*Hips.*—None observed.

Plants:

*Habit.*—Upright, compact, well branched, forming a rounded mound.

*Growth.*—Vigorous, 18 to 22 inches tall and up to a foot spread at maturity.

*Foliage.*—Small, compound of mostly three to five (sometimes seven) leaflets. Color: new foliage, upper surface — near 146B; under side — near 146D. Old foliage, upper surface — near 147A; under side — near 147B.

*Leaflet.*—Shape — ovate with acute tip; texture, upper surface — satiny, underside — matte; edge — fine, even serration.

*Rachis.*—Color, upper surface — near 147C, under side — near 146C; occasionally one or two prickles on under side of leaf stem.

*Stipules.*—Very finely bearded, attached to the stem for 5/16 of an inch, then curling outward for ⅛ of an inch.

*New wood.*—Smooth with a color near 146B.

*Old wood.*—Near 143C in color, the oldest wood becoming covered with near 200C, and still smooth.

*Resistance to diseases.*—Good.

*Thorns.*—On main stalk: few. On laterals from main stalk: averaging six per inch in an irregular manner; up to ¼ of an inch in length; color near 166A when young, becoming 165B and finally 165C; very thin and straight, occasionally angled downward slightly.

*Prickles.*—Only one or two on the main stem of the leaf.

The miniature rose plant and its flowers described herein may vary in detail due to climate, soil and cultural conditions under which the variety may be grown; the present description being of the new variety as grown outside in Essex County, Mass. in early September.

The following is claimed:

1. A new and distinct variety of miniature rose plant of hardy, upright, well branched, compact habit, substantially as illustrated and described, characterized by buds and flowers of an apricot blend, borne in clusters but also singly making them ideal for cut flowers; and further characterized by a plant of vigorous growth, being good as a hardy graden perennial, easy to propagate from cuttings, with an abundant amount of medium green foliage.

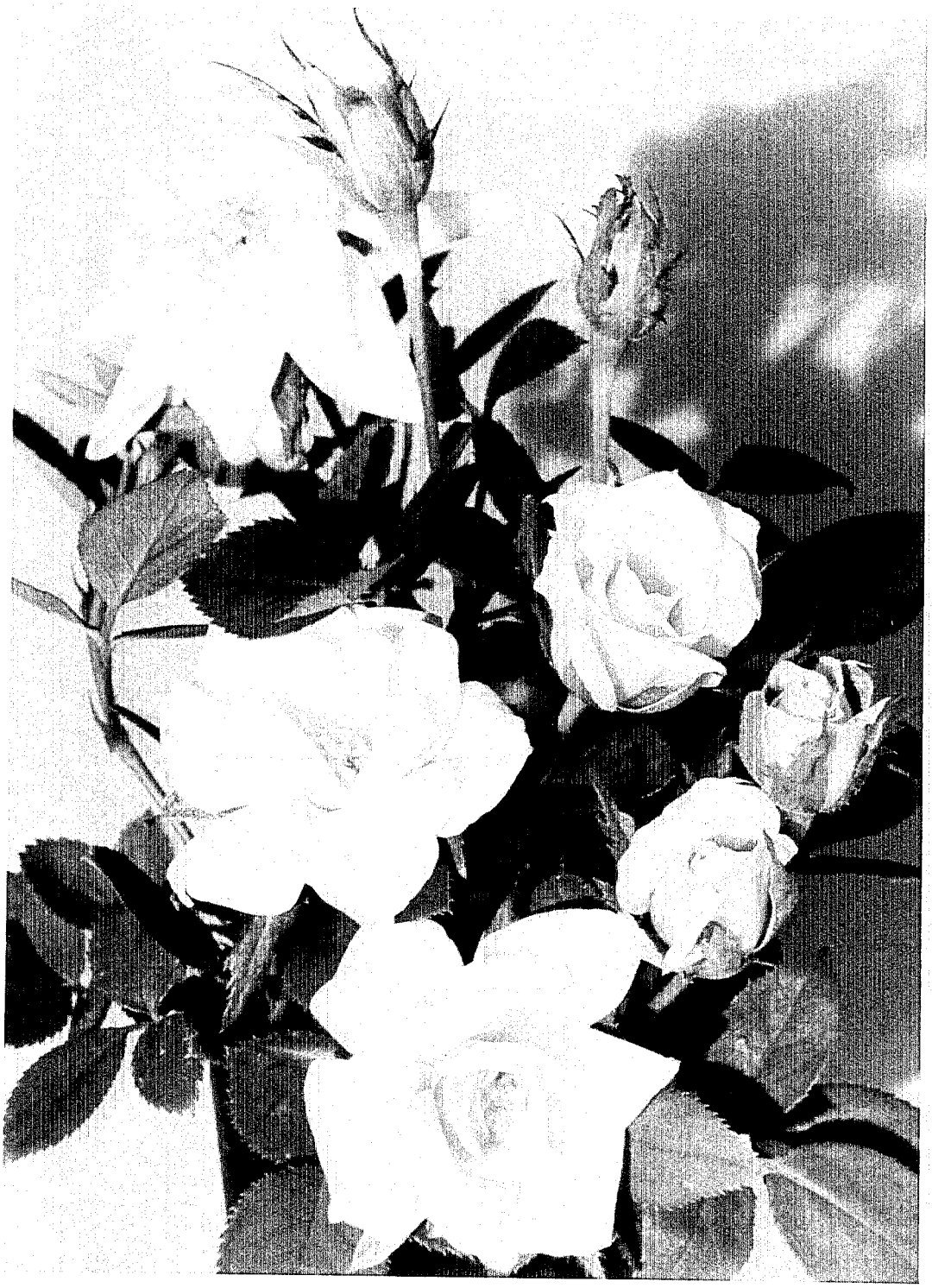

* * * * *